United States Patent
Yang

(10) Patent No.: US 11,147,486 B2
(45) Date of Patent: Oct. 19, 2021

(54) ONE STEP ALL-IN-ONE APPARATUS FOR BODY FLUID SAMPLING AND SENSING

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 381 days.

(21) Appl. No.: 16/321,858

(22) PCT Filed: Aug. 12, 2016

(86) PCT No.: PCT/CN2016/094947
§ 371 (c)(1),
(2) Date: Jan. 30, 2019

(87) PCT Pub. No.: WO2018/027930
PCT Pub. Date: Feb. 15, 2018

(65) Prior Publication Data
US 2019/0175086 A1  Jun. 13, 2019

(51) Int. Cl.
*A61B 5/151* (2006.01)
*A61B 5/15* (2006.01)
(Continued)

(52) U.S. Cl.
CPC ............ *A61B 5/157* (2013.01); *A61B 5/1455* (2013.01); *A61B 5/15* (2013.01); *A61B 5/151* (2013.01);
(Continued)

(58) Field of Classification Search
CPC ........... A61B 5/145; A61B 5/157; A61B 5/15; A61B 5/15159; A61B 5/150358; A61B 5/150244; A61B 5/150022
See application file for complete search history.

(56) References Cited

U.S. PATENT DOCUMENTS

| 2003/0212344 A1 | 11/2003 | Yuzhakov et al. |
| 2006/0008389 A1 | 1/2006 | Sacherer et al. |

(Continued)

FOREIGN PATENT DOCUMENTS

| CN | 1456888 A | 11/2003 |
| CN | 101583306 A1 | 11/2009 |

(Continued)

OTHER PUBLICATIONS

Machine translation of CN103829953A from Google Patents: https://patents.google.com/patent/CN103829953A/en (Year: 2014).*
European Patent Application No. 16912385.8; Extended Search Report; dated Feb. 12, 2020; 7 pages.

*Primary Examiner* — Eric F Winakur
*Assistant Examiner* — Jasim Ahmad Naeem
(74) *Attorney, Agent, or Firm* — JCIP Global Inc.

(57) ABSTRACT

A one step all-in-one apparatus for body fluid sampling and sensing, comprising: a housing(1), a plurality of integrated sampling and sensing assemblies, a cartridge(12), sealing films(101,102), an upper cover(13), a sampling port(6), a linear actuating mechanism and a control circuit, with every integrated sampling and sensing assembly comprising a micro fluid-sampling needle(2), a needle hub(3) and a test strip(4); the micro fluid-sampling needles(2) penetrate the skin to sample the body fluid and deliver the body fluid to the test strips(4) directly, and changes occurred on the test strips(4) are read by the sensor(5), wherein sampling and sensing are completed in one step. The sealing films(101, 102) and a plurality of chambers(15) of the cartridge(12) compose sealed reaction chambers(15) and the linear actuating mechanism which is connected with the control circuit electrically drives the integrated sampling and sensing assemblies allowing the micro sampling needles(2) to penetrate the skin and reach the designated depths under the skin. The one step all-in-one apparatus for body fluid
(Continued)

sampling and sensing has advantages as small size, high efficiency, convenient operation, short time consumption, less fluid consumption, depth-controllable penetration, and accurate and reliable results.

12 Claims, 3 Drawing Sheets

(51) Int. Cl.
  *A61B 5/1455* (2006.01)
  *A61B 5/157* (2006.01)
  *A61B 5/00* (2006.01)
(52) U.S. Cl.
  CPC .... *A61B 5/150022* (2013.01); *A61B 5/15117* (2013.01); *A61B 5/15159* (2013.01); *A61B 5/150244* (2013.01); *A61B 5/150358* (2013.01); *A61B 5/742* (2013.01); *A61B 5/7475* (2013.01)

(56) References Cited

U.S. PATENT DOCUMENTS

| | | | |
|---|---|---|---|
| 2008/0167578 | A1 | 7/2008 | Bryer et al. |
| 2010/0021947 | A1* | 1/2010 | Emery ............... A61B 5/15163 435/14 |
| 2010/0286560 | A1* | 11/2010 | Freeman .......... A61B 5/150427 600/583 |
| 2013/0172698 | A1 | 7/2013 | Reynolds et al. |

FOREIGN PATENT DOCUMENTS

| | | |
|---|---|---|
| CN | 103829953 A | 6/2014 |
| CN | 205433702 U | 8/2016 |
| CN | 106137223 A | 11/2016 |
| JP | H05317426 A | 12/1993 |
| WO | WO 2004/064636 A1 | 8/2004 |
| WO | WO 2013/020103 A1 | 2/2013 |

\* cited by examiner

ONE STEP ALL-IN-ONE APPARATUS FOR BODY FLUID SAMPLING AND SENSING

CROSS-REFERENCE TO RELATED APPLICATIONS

This application is the National Stage of International Patent Application No. PCT/CN2016/094947, filed Aug. 12, 2016, the disclosure of which is incorporated herein by reference in its entirety.

TECHNICAL FIELD

The present invention generally relates to the field of medical appliance, more particularly, to a one step all-in-one apparatus for body fluid sampling and sensing.

BACKGROUND OF THE INVENTION

After the portable blood glucose meter was invented in the 1970s, patients can self-test blood sugar and get the outcome very soon. According to the portable blood glucose meter in the market, the procedure of blood glucose measurement usually consists of several steps: firstly, the patient needs to penetrate his or her skin with a lancet, secondly, smear the blood directly or use a blood sampling device to apply a blood drop onto a blood glucose test strip, finally the blood glucose level is interpreted by a blood glucose meter. This kind of testing procedure has disadvantages as large amount of sampling blood, considerable pain of the patient, tedious members and complicated steps. Moreover, the accuracy of blood glucose test strips applied separately from the lancets is easily influenced by environmental factors such as temperature, humidity, chemicals and etc., blood glucose test strips stored in an environment that is cold, hot, humid or polluted, or expired blood glucose test strips can negatively affect the accuracy of the measured blood glucose level.

To solve the problems identified above, modern blood glucose meters appeared on the current market, with the sensor, the blood glucose test strips and the sampling member located in one body, which area progress compared to conventional split glucose meters. However, the lancet and the blood glucose test strip still work as independent parts in operations, meaning the patient still needs to prick a finger tip by a lancet and put the finger tip near a blood glucose test strip, then wait or press around the wound until enough blood for testing is delivered to the blood glucose test strip, then wait for the reaction between the blood and the reagents on the test strips, eventually the result data will be interpreted by the glucose meter, in which way the operation in not only time and energy consuming, but also very inconvenient.

In terms of driving the lancet, the prior art has made some attempts. The most commonly used actuator to drive the lancet is a spring, for instance, a torsion spring to drive the lancet in an arcuate path to realize penetration and withdrawal of the lancet. But this kind of actuation is not linear, and the depth and angle of the penetration is not fixed and cannot be predetermined, bringing safety risks to the patient.

In terms of sampling blood with a sampling member, the prior arts involve hollow sampling members similar to the micro sampling needles in the present invention, and the exit of the sampling member described in the prior arts was connected directly with a vacuum device. However, this way of connection is hard to be repeated by the patients themselves so the used blood sampling members cannot be easily replaced resulting in impossibility of multiple testing using a plurality of testing units in a cartridge, which is not practical in daily blood glucose testing.

In terms of the sensors, electrochemical sensors and optical sensors are commonly applied in the blood glucose meters, but traditional electrochemical sensors have shortcomings as lack of precision and traditional optical sensors have shortcomings as long testing time. Under the hypothetical condition of completing sampling and sensing in one-step operation and obtaining the test result in a short time, the optical sensors have considerable advantages and vaster applications in the technical field of analyte detection.

SUMMARY OF THE INVENTION

Regarding the above-mentioned shortcomings of the prior art, the present invention provides a one step all-in-one apparatus for body fluid sampling and sensing, comprising: a housing, a plurality of integrated sampling and sensing assemblies, a cartridge, sealing films, an upper cover, a sampling port, a linear actuating mechanism, a control circuit and withdrawing springs.

One integrated sampling and sensing assembly comprises a micro fluid-sampling needle, a needle hub and a test strip; the micro fluid-sampling needle is fixed on the needle hub, and the test strip is mounted on the lower surface of the needle hub, and a hole is set on the needle hub to enable the communication between the micro fluid-sampling needle and the test strip, and the plurality of integrated sampling and sensing assemblies are arranged in a radial configuration in the cartridge.

The micro fluid-sampling needles are hollow microneedles, configured to penetrate the skin to sample the body fluid and deliver the body fluid to the test strips directly via the holes on the needle hubs, and the sensor is configured to read the changes occurred on the test strips due to the reaction of the body fluid with the reagents on the test strips, wherein sampling and sensing are completed in one step.

The sealing films are located on the upper and lower surfaces of the cartridge respectively, and a plurality of chambers are arranged in a radial configuration in the cartridge, wherein the upper and lower sealing films and the plurality of chambers compose a plurality of sealed reaction chambers.

The upper cover is located on the upper portion of the housing, and the sampling port is located on the upper cover, configured to allow the micro sampling needle protrude from and withdraw into the housing.

The linear actuating mechanism which is connected with the control circuit electrically is located below the cartridge, configured to actuate the integrated sampling and sensing assemblies allowing the micro sampling needles to penetrate the skin.

The control circuit is configured to control the movements of the linear actuating mechanism and the integrated sampling and sensing assemblies so as to control the micro sampling needles to reach the designated depths under the skin.

The withdrawing springs are set in the plurality of chambers, configured to withdraw the micro sampling needles after sampling.

Alternatively, the linear actuating mechanism comprises a rod and a rod spring. The rod is a hollow rod, and a side hole is set on one end of the rod near the cartridge, configured to connect the lumen of the rod and the sealed reaction chamber after the rod penetrates the sealing film on the lower surface of the cartridge.

A vacuum device is set on the other end of the rod away from the cartridge;

The rod spring is configured to withdraw the rod after sampling of the body fluid of the integrated sampling and sensing assembly.

Alternatively, the one step all-in-one apparatus for body fluid sampling and sensing further comprises a block ring assembly.

The block ring assembly comprises a block ring and a block ring spring.

The block ring wraps the outer surface of the rod annularly, configured to block the breakage on the sealing film on the lower surface of the cartridge when the film is penetrated by the rod to maintain the sealed condition of the sealed reaction chamber.

The block ring spring is configured to press the block ring against the sealing film tight when blocking the breakage on the sealing film.

Alternatively, the block ring is a silicone ring.

Alternatively, the outer diameter of the micro sampling needle is 50~500 um. Alternatively, the sensor is an optical sensor, configured to read an optically readable signal produced upon the reaction of the reagents on the test strip with the analyte present in the sampled body fluid.

One test time from sampling by the integrated sampling and sensing assembly to generating result data by the optical sensor is 5-10s.

Alternatively, an annular wall is located in the center of the cartridge, and a rotatable member is set on the housing.

Alternatively, the one step all-in-one apparatus for body fluid sampling and sensing further comprises a sensing circuit, configured to sense whether a body part to be sampled is at the designated position or not.

An annular wall is located in the center of the cartridge, and a rotatable member is set on the housing;

An internal gear is set on the annular wall, an external gear is set on the rotatable member which can be engaged with the cartridge by meshing the gears, configured to rotate the cartridge in the receiving tank in the housing.

Alternatively, multiple protruding guide structures are set in every chamber of the cartridge, and multiple holes with shapes matching the guide structures are set on the needle hubs, configured to keep the longitudinal movement and limit the non-longitudinal movement of the needle hubs along the guide structures in the chambers.

Alternatively, a hole is set on the top surface of every chamber, configured to let passing of the micro sampling needle.

Alternatively, the number of the chambers is 2~50.

Alternatively, the number of the chambers is 10.

Alternatively, a magnet is located on the inner surface of the upper cover, and a magnet sensor is set in the housing, configured to connect the magnet magnetically to test whether the upper cover is tightly closed as intended.

Alternatively, the one step all-in-one apparatus for body fluid sampling and sensing further comprises a display screen.

The display screen is located in the upper half of the housing, configured to display the result data;

Alternatively, at least one button is set next to the display screen, configured to receive control instructions from the user.

The one step all-in-one apparatus for body fluid sampling and sensing in the present invention applies a unique structure of an integrated sampling and sensing assembly integrating a micro sampling needle, a test strip and a needle hub in every chamber of the cartridge, with the sampling needle drawing a body fluid from a human body and delivering the body fluid to the test strip directly, then an optically readable signal produced upon the reaction of the reagents on the test strip with the analyte present in the sampled body fluid is read by the optical sensor. Sampling and sensing of body fluids are completed in one step without pressing around the wound or waiting a long time after penetration to sample enough body fluid to test, which not only saves testing time and testing fluid, but also minimizes the pain of the patient. The one step all-in-one apparatus for body fluid sampling and sensing in the present invention uses a cartridge comprising a plurality of chambers with every integrated sampling and sensing assembly located in every chamber, so that the replacement of the cartridge happens after multiple tests instead of one, and the frequency of replacement is largely decreased. Moreover, the chambers and the upper and lower sealing films in the present invention constitute a plurality of sealed reaction chambers, maintaining the sealed condition of the sealed reaction chambers during sampling with the assistance of a sealing silicone ring, which enhances the effectiveness of the sampling procedure by creating vacuum in the sealed reaction chambers. Last but not least, the micro sampling needles in the present invention are driven by a linear actuator which is controlled by a control circuit, enabling adjustments of depths of the penetration of the needles according to different skin thicknesses of the patients. At the same time, the diameter of the micro sampling needles in the present invention is tiny, which minimizes the pain of the patient while ensuring the sampling amount. In summary, the one step all-in-one apparatus for body fluid sampling and sensing in the present invention has advantages of small size, high efficiency, convenient operation, short time consumption, less fluid consumption, depth-controllable penetration, accurate and reliable results, meeting the patients' needs for fast and accurate measurement of the amount of analytes in the body fluid with minimized pain.

DETAILED DESCRIPTION

To make the above-mentioned objects, features and advantages of the present invention more obvious and understandable, the embodiments of the present invention are described in the following through specific embodiments.

Figure 1:
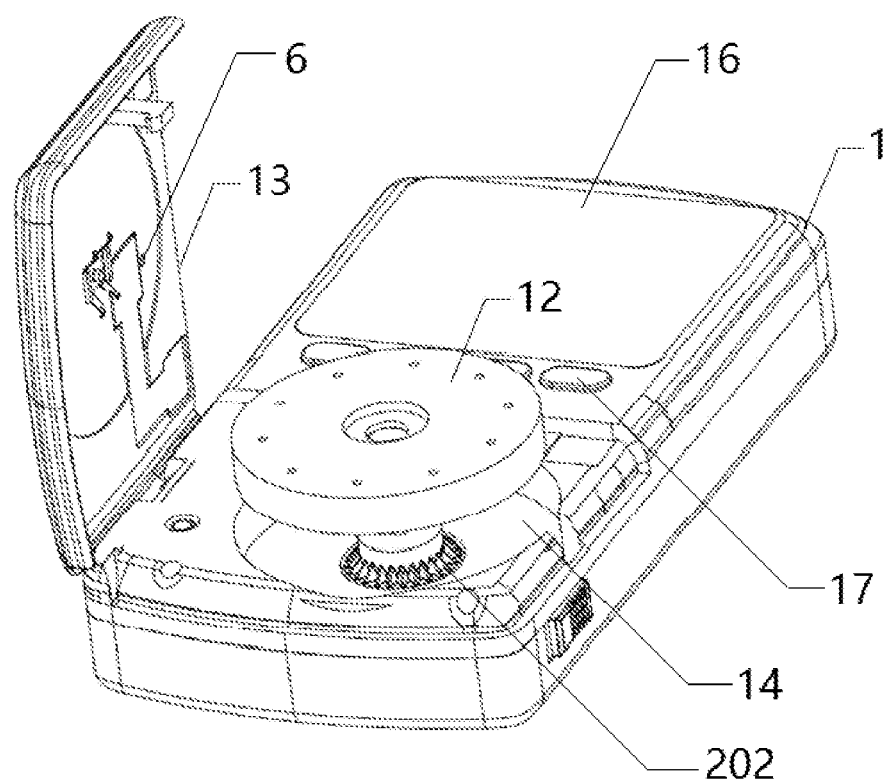
FIG. 1 illustrates a perspective view of an embodiment of a one step all-in-one apparatus for body fluid sampling and sensing in the present invention.
Figure 2:
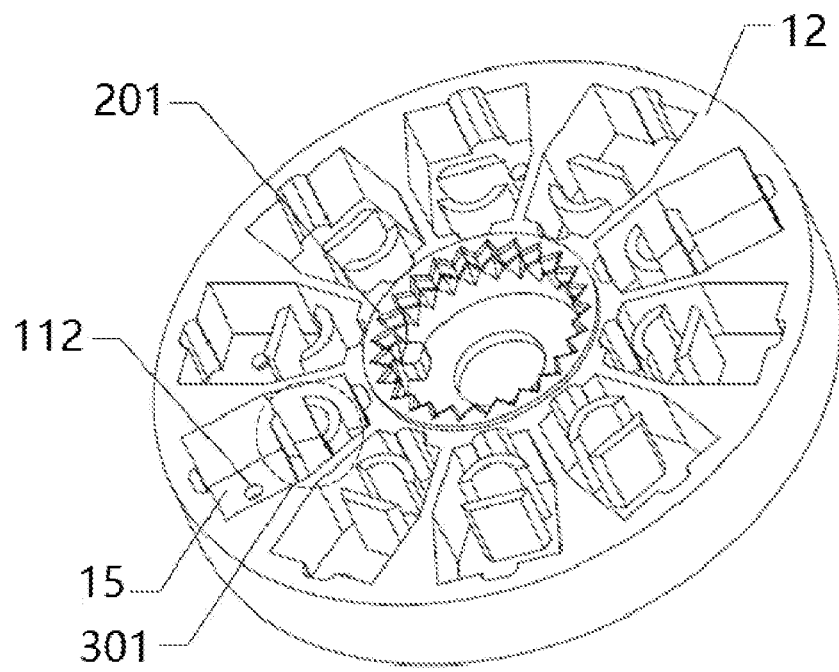
FIG. 2 illustrates a perspective view of a cartridge of the one step all-in-one apparatus for body fluid sampling and sensing in the present invention.

Referring to the FIG. 1 and FIG. 2, provided is an exemplary embodiment of a one step all-in-one apparatus for body fluid sampling and sensing in the present invention, comprising: a housing 1, and an upper cover 13 is located on the upper portion of the housing 1, and a container 14 is located in the housing 1 which is configured to contain the cartridge 12, and a rotatable member 202 is located in the container 14 which can be engaged with an internal gear on the annular wall 201 of the cartridge 12, and a display screen 16 and several buttons 17 are set on the housing 1. Open the upper cover 13, the cartridge 12 can be put in or taken out of the container 14. After putting the cartridge 12 in, the internal gear on its annular wall 201 can be engaged with the external gear on the rotatable member 202, which rotates the cartridge 12 in the container 14 in a circumferential direction. Result data produced by the sensor is displayed on the display screen 16 after sampling and sensing, and several buttons 17 are set next to the display screen 16 to receive control instructions from the user.

Figure 3:
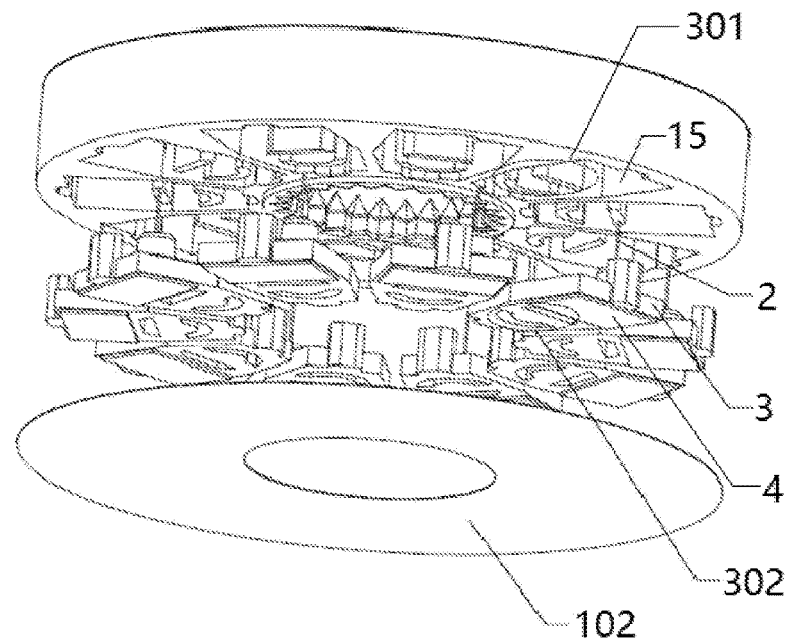
FIG. 3 illustrates a perspective assembly drawing of the cartridge of the one step all-in-one apparatus for body fluid sampling and sensing in the present invention.

Referring to the FIG. 2 and FIG. 3, provided is an exemplary embodiment of a match pattern of the cartridge 12 and the integrated sampling and sensing assemblies in the present invention. In this embodiment, ten chambers 15 are set inside the cartridge 12, and an annular wall 201 is set in the center of the cartridge 12. The internal gear on the annular wall 201 can be engaged with the external gear on the rotatable member 202 configured to realize the rotation of the cartridge 12 in the container 14. A hole 112 is set on the top surface of every chamber 15, through which a micro sampling needle 2 can protrude from the cartridge 12 when a sampling is needed and withdraw into the cartridge 12 after a sampling is completed. Furthermore, multiple protruding guide structures 301 are set in every chamber 15 of the cartridge 12, and multiple holes 302 with their shapes matching the guide structures 301 are set on a needle hub 3 of every integrated sampling and sensing assembly, configured to keep the longitudinal movement and limit the non-longitudinal movement of the needle hubs 3 along the guide structures 301 in the chambers 15 to ensure the control of the motion path of the micro sampling needle 2.

Figure 4:
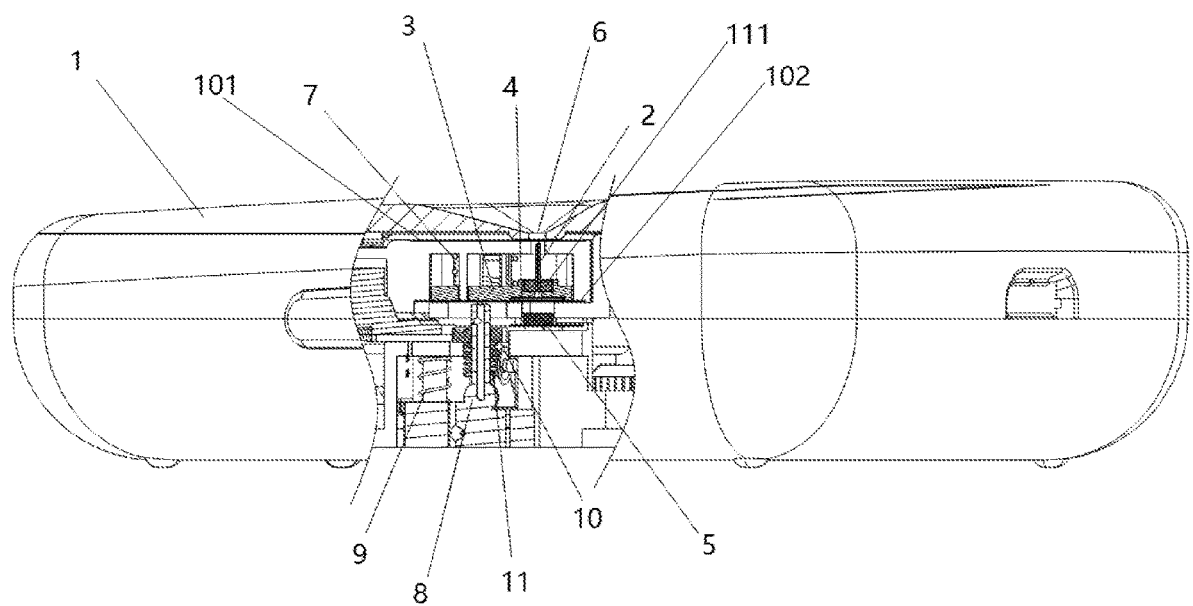
FIG. 4 illustrates a partial cross-sectional view of the one step all-in-one apparatus for body fluid sampling and sensing in the present invention.

Referring to the FIG. 3 and FIG. 4, provided is an exemplary embodiment of an assembly method of the cartridge 12, the plurality of integrated sampling and sensing assemblies each comprising the micro sampling needle 2, the needle hub 3 and a test strip 4, and a lower sealing film 102. The micro sampling needle 2 is fixed on the needle hub 3 via a fixing structure, and the test strip 4 is mounted on the lower surface of the needle hub 3, and a hole 111 is set on the needle hub to enable the communication between the micro sampling needle 2 and the test strip 4, and multiple holes 302 with their shapes matching the guide structures 301 in every chamber 15 are set on every needle hub 3. Every integrated sampling and sensing assembly comprising a micro sampling needle 2, a needle hub 3 and a test strip 4 is assembled in every chamber 15 of the cartridge 12. A lower sealing film 102 is sealed on the lower surface of the cartridge 12 and an upper sealing film 101 is sealed on the upper surface cartridge 12 after assembling so the chambers 15 and the sealing films 101, 102 compose a plurality of sealed reaction chambers.

Referring to the FIG. 1 to FIG. 4, provided is an exemplary embodiment of a way of driving the integrated sampling and sensing assemblies in the present invention. Every integrated sampling and sensing assembly comprising a micro sampling needle 2, a needle hub 3 and a test strip 4 is assembled in every chamber 15 of the cartridge 12, and a hole 111 is set on the needle hub to enable the communication between the micro sampling needle 2 and the test strip 4. A withdrawing spring 7 is further set between the top surface of the cartridge 12 and the needle hub 3 in every chamber 15. The sealing films 101, 102 are sealed on the upper and lower surfaces of the cartridge 12 respectively, and compose a plurality of sealed reaction chambers with the chambers 15. An optical sensor 5 is located below the cartridge 12 in the housing 1, and a sampling port 6 is located on the upper cover 13.

In this embodiment, a linear actuating mechanism configured to drive the integrated sampling and sensing assemblies comprising a rod 8 and a rod spring 9 is located below the cartridge 12 in the housing 1. In this embodiment, the rod 8 is a hollow rod, and a side hole is set on one end of the rod 8 near the cartridge 12, and a vacuum device is set on the other end of the rod 8 away from the cartridge 12, and a rod spring 9 is located near the rod 8. In this embodiment, a block ring assembly comprising a block ring 10 and a block ring spring 11 is further set in the housing 1. The block ring 10 wraps the outer surface of the rod 8 annularly, the upper end of the block ring spring 11 is connected with the block ring 10 and the lower end of the block ring spring 11 is connected with the rod 8. The rod 8 is electrically connected with a control circuit.

When a sampling is needed, the rod 8 rises under the control of the control circuit, penetrating the transparent lower sealing film 102 on the lower surface of the cartridge 12, contacting the needle hub 3 and driving the whole integrated sampling and sensing assembly moving upward, during which the rod spring 9 and the withdrawing spring 7 are both compressed from their initial state to a compressed state. The micro sampling needle 2 rises with the integrated sampling and sensing assembly, penetrating the upper sealing film 101 on the upper surface of the cartridge 12, going through the sampling port 6 on the upper cover 13, and penetrating a human skin eventually. When the micro sampling needle 2 reaches a designated depth under the skin, the control circuit stops the rod 8 from further rising, so the movement of integrated sampling and sensing assembly is stopped accordingly. During the rising of the rod 8, the block ring 10 rises with the rod 8, and the block ring spring 11 is at its initial state. After the rod 8 penetrating the lower sealing film 102, the block ring 10 contacts the lower sealing film 102 and blocks the breakage on the lower sealing film 102 around the rod 8. After the block ring 10 contacting the lower sealing film 102, the rod 8 rises further, and the block ring spring 11 compresses to press the block ring 10 against the lower sealing film 102 tight. The micro sampling needle 2 penetrates the upper sealing film 101 during its rising too, but due to a tiny diameter of the micro sampling needle 2 from 50 μm to 500 μm, no breakage is likely to occur on the upper sealing film 101 around the needle. Due to the sealing of the breakage on the lower sealing film 102 by the block ring 10, the sealed condition of the sealed reaction chambers consisting of the chambers 15 and the sealing films 101, 102 is maintained.

When the micro sampling needle 2 reaches the designated depth under the skin, the side hole on the rod 8 is inside the sealed reaction chamber and above the lower sealing film 102, communicating the lumen of the rod 8 and the sealed reaction chamber. The vacuum device generates a vacuum in the lumen of the rod 8, and thus a vacuum in the sealed reaction chamber due to its communication with the lumen of the rod 8. The micro sampling needle 2 in this embodiment is a hollow microneedle, so there is also a vacuum generated in the lumen of the hollow microneedle, which helps the hollow microneedle sample a body fluid after penetrating the skin.

When enough body fluid is sampled, the micro sampling needle 2 delivers the body fluid to the test strip 4 mounted on the needle hub 3 directly via the hole 111 on the needle hub 3, and the analyte in the body fluid reacts with the reagents on the test strips 4 producing a color change on the test strip 4. The color change as an optically readable signal is read by the optical sensor 5 which is located below the cartridge 12, and a result data is generated accordingly which is to be displayed on the display screen 16. The sampling and sensing processes are completed in one step which costs only 5 to 10 seconds without any interference from the user needed.

During the sampling procedure, the rod 8 rises under the control of the control circuit, and the rod spring 9 is at its compressed state; the integrated sampling and sensing assembly is driven upward by the rod 8, and the withdrawing spring 7 is also at its compressed state. When the micro sampling needle 2 reaches the designated depth under the skin, the rod 8 stops under the control of the control circuit, at this time, the need of restoring the initial state from the compressed state of the rod spring 9 releases the rod spring 9, and the tension released from the rod spring 9 withdraws the rod 8 back to its initial state. In the process of withdrawing the rod 8, the block ring spring 11 releases tension, restores the initial state from the compressed state, and is no longer tightly pressing the block 10 against the lower sealing film 102. After sampling, the withdrawing spring 7 also restores the initial state from the compressed state, and the tension released accordingly withdraws the micro sampling needle 2 back into the housing 1.

When one integrated sampling and sensing assembly is used, the cartridge 12 is rotated by a circumferential distance of one chamber to make a new integrated sampling and sensing assembly on standby in the designated position. In this embodiment, a cartridge 12 comprises ten chambers 15 and thus ten corresponding integrated sampling and sensing assemblies, which means ten times of sampling and sensing. The cartridge 12 needs to be changed after ten times of sampling and sensing, which is convenient to use.

Figure 5:
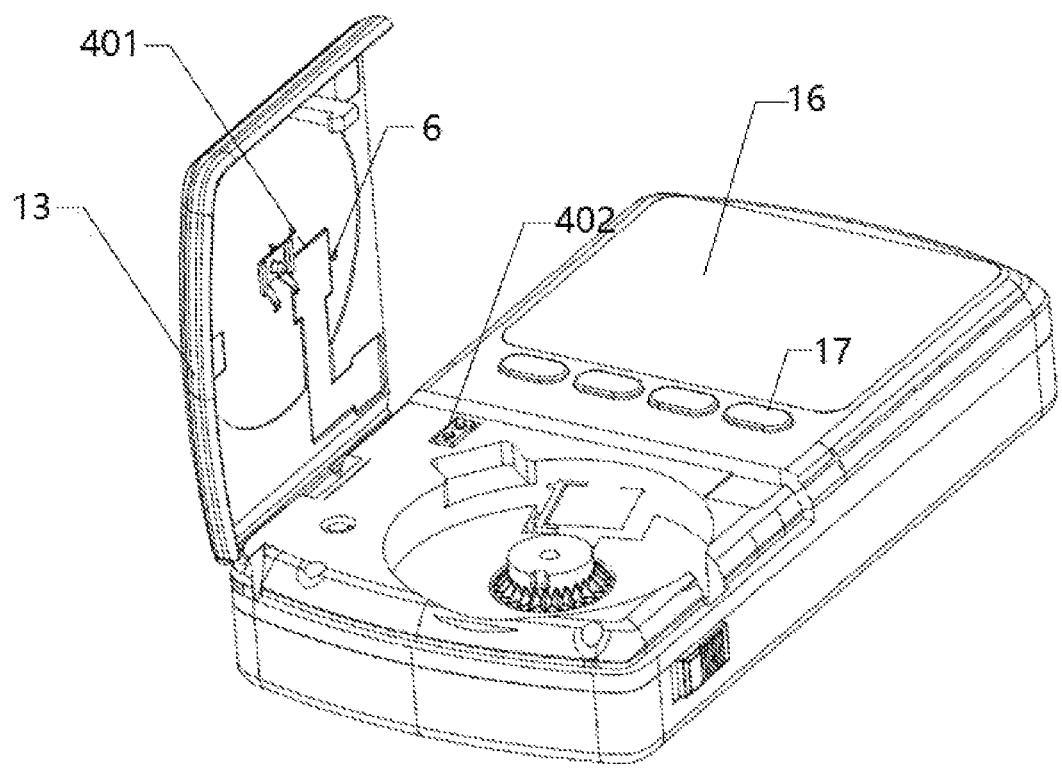
FIG. 5 illustrates a perspective view of another embodiment of the one step all-in-one apparatus for body fluid sampling and sensing in the present invention.
Figure 6:
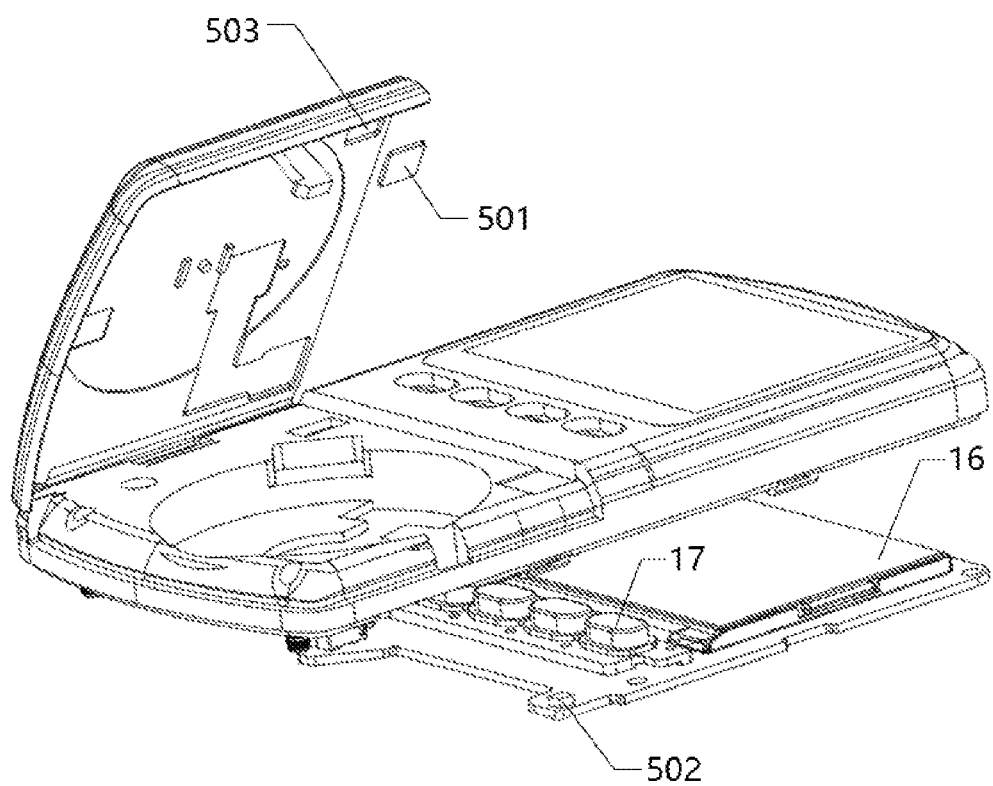
FIG. 6 illustrates an exploded view of another embodiment of the one step all-in-one apparatus for body fluid sampling and sensing in the present invention.

Referring to the FIG. 5, in this embodiment, a sensing circuit 401 configured to sense whether a body part to be sampled is at the designated position or not is further set on the inner surface of the upper cover 13, and a connector 402 is set in the housing 1 which can contact and be electrically connected with the sensing circuit 401 when the upper cover 13 is closed, and the connector 402 is also electrically connected with the control circuit controlling the linear actuating mechanism. In this embodiment, the connector 402 is a telescopic probe, and when the upper cover 13 is closed, the metal wire of the sensing circuit 401 is pressed on the telescopic probe to realize the electrical connection with the control circuit, so the sensing circuit 401 can send an electrical signal to the control circuit to control the linear actuating mechanism driving the micro sampling needle 2 going through the sampling port 6 to sample a body fluid when sensing a body part.

The above descriptions of the detailed embodiments are only to illustrate the principle and the effect of the present invention, and it is not to limit the scope of the present invention. Those skilled in the art can modify or change the embodiments without departing from the spirit and scope of the present invention. Accordingly, all equivalent modifications and variations completed by persons of ordinary skill in the art, without departing from the spirit and technical idea of the present invention, should fall within the scope of the present disclosure defined by the appended claims.

The invention claimed is:

1. A one step all-in-one apparatus for body fluid sampling and sensing, comprising:
a housing, a plurality of integrated sampling and sensing assemblies, a cartridge, sealing films, an upper cover, a sampling port, a linear actuating mechanism, a control circuit and withdrawing springs;
wherein,
each integrated sampling and sensing assembly comprises a micro sampling needle, a needle hub and a test strip; the micro sampling needle is fixed on the needle hub, and the test strip is mounted on the lower surface of the needle hub, and a hole is set on the needle hub to enable the communication between the micro sampling needle and the test strip, and the plurality of integrated sampling and sensing assemblies are arranged in a radial configuration in the cartridge;
the micro sampling needles are hollow microneedles, configured to penetrate the skin to sample the body fluid and deliver the body fluid to the test strips directly via the holes on the needle hubs, and a sensor is configured to read the changes occurred on the test strips due to the reaction of the body fluid with the reagents on the test strips, wherein sampling and sensing are completed in one step;
the sealing films are located on the upper and lower surfaces of the cartridge respectively, and a plurality of chambers are arranged in a radial configuration in the cartridge, wherein the upper and lower sealing films and the plurality of chambers compose a plurality of sealed reaction chambers;
the upper cover is located on the upper portion of the housing, and the sampling port is located on the upper cover, configured to allow the micro sampling needle protrude from and withdraw into the housing;
the linear actuating mechanism which is connected with the control circuit electrically is located below the cartridge, configured to actuate the integrated sampling and sensing assemblies allowing the micro sampling needles to penetrate the skin,
wherein the linear actuating mechanism comprises a rod and a rod spring,
the rod is a hollow rod, and a side hole is set on one end of the rod near the cartridge, configured to connect the lumen of the rod and the sealed reaction chamber after the rod penetrates the sealing film on the lower surface of the cartridge;
a vacuum device is set on the other end of the rod away from the cartridge; and
the rod spring is configured to withdraw the rod after sampling of the body fluid of the integrated sampling and sensing assembly;
the control circuit is configured to control the movements of the linear actuating mechanism and the integrated sampling and sensing assemblies so as to control the micro sampling needles to reach the designated depths under the skin;
the withdrawing springs are set in the plurality of chambers, configured to withdraw the micro sampling needles after sampling.

2. The one step all-in-one apparatus for body fluid sampling and sensing according to claim 1, further comprising a block ring assembly,
the block ring assembly comprises a block ring and a block ring spring, the block ring wraps the outer surface of the rod annularly, configured to block the breakage on the sealing film on the lower surface of the cartridge when the film is penetrated by the rod to maintain the sealed condition of the sealed reaction chamber;

the block ring spring is configured to press the block ring against the sealing film tight when blocking the breakage on the sealing film.

3. The one step all-in-one apparatus for body fluid sampling and sensing according to claim 2, wherein, the block ring is a silicone ring.

4. The one step all-in-one apparatus for body fluid sampling and sensing according to claim 1, wherein, the outer diameter of the micro sampling needle is ranged from 50 um to 500 um.

5. The one step all-in-one apparatus for body fluid sampling and sensing according to claim 1, wherein, the sensor is an optical sensor, configured to read an optically readable signal produced upon the reaction of the reagents on the test strip with the analyte present in the sampled body fluid, one testing time from sampling by the integrated sampling and sensing assembly to generating result data by the optical sensor is ranged from 5s to 10s.

6. The one step all-in-one apparatus for body fluid sampling and sensing according to claim 1, further comprising a sensing circuit, configured to sense whether a body part to be sampled is at the designated position or not.

7. The one step all-in-one apparatus for body fluid sampling and sensing according to claim 1, wherein, an annular wall is located ill the center of the cartridge, and a rotatable member is set on the housing;

an internal gear is set on the annular wall, an external gear is set on the rotatable member which can be engaged with the cartridge by meshing the gears, configured to rotate the cartridge in a receiving tank in the housing.

8. The one step all-in-one apparatus for body fluid sampling and sensing according to claim 1, wherein, multiple protruding guide structures are set in every chamber of the cartridge, and multiple holes with shapes matching the guide structures are set on the needle hubs, configured to keep the longitudinal movement and limit the non-longitudinal movement of the needle hubs along the guide structures in the chambers;

a hole is set on the top surface of every chamber, configured to let passing of the micro sampling needle.

9. The one step all-in-one apparatus for body fluid sampling and sensing according to claim 1, wherein, the number of the chambers is ranged from 2 to 50.

10. The one step all-in-one apparatus for body fluid sampling and sensing according to claim 9, wherein, the number of the chambers is 10.

11. The one step all-in-one apparatus for body fluid sampling and sensing according to claim 1, wherein, a magnet is located on the inner surface of the upper cover, and a magnet sensor is in the housing is configured in corresponding to the magnet to test whether the upper cover is tightly closed as intended.

12. The one step all-in-one apparatus for body fluid sampling and sensing according to claim 1, further comprising a display screen, the display screen is located in the upper half of the housing, configured to display result data;

at least one button is set next to the display screen, configured to receive control instructions from the user.

* * * * *